US008697080B2

(12) United States Patent
Goldenberg et al.

(10) Patent No.: US 8,697,080 B2

(45) Date of Patent: Apr. 15, 2014

(54) METHODS AND COMPOSITIONS FOR TREATMENT OF HUMAN IMMUNODEFICIENCY VIRUS INFECTION WITH CONJUGATED ANTIBODIES OR ANTIBODY FRAGMENTS

(71) Applicant: Immunomedics, Inc., Morris Plains, NJ (US)

(72) Inventors: David M. Goldenberg, Mendham, NJ (US); Chien-Hsing Chang, Downingtown, PA (US); Edmund A. Rossi, Morris Plains, NJ (US); William J. McBride, Boonton, NJ (US)

(73) Assignee: Immunomedics Inc., Morris Plains, NJ (US)

( * ) Notice: Subject to any disclaimer, the term of this patent is extended or adjusted under 35 U.S.C. 154(b) by 0 days.

(21) Appl. No.: 13/675,422

(22) Filed: Nov. 13, 2012

(65) Prior Publication Data

US 2013/0071406 A1 Mar. 21, 2013

Related U.S. Application Data

(62) Division of application No. 11/745,692, filed on May 8, 2007, now Pat. No. 8,333,971.

(60) Provisional application No. 60/800,342, filed on May 15, 2006.

(51) Int. Cl.
*A61K 39/00* (2006.01)
*A61K 39/395* (2006.01)

(52) U.S. Cl.
USPC .................................................. 424/178.1

(58) Field of Classification Search
None
See application file for complete search history.

(56) References Cited

U.S. PATENT DOCUMENTS

| | | | | |
|---|---|---|---|---|
| 6,706,252 | B1 | 3/2004 | Ericsson et al. | |
| 2004/0241158 | A1* | 12/2004 | McBride et al. | 424/130.1 |
| 2005/0175619 | A1 | 8/2005 | Duffy et al. | |
| 2006/0193865 | A1* | 8/2006 | Govindan | 424/155.1 |

FOREIGN PATENT DOCUMENTS

| | | |
|---|---|---|
| WO | 9110742 | 7/1991 |
| WO | 9111198 | 8/1991 |

OTHER PUBLICATIONS

Armbruster et al., "Passive immunization with the anti-HIV-1 human monoclonal antibody (hMAb) 4E10 and the hMAb combination 4E1012F512G12", J Antimicrob Chemother. Nov. 2004;54(5):915-20.

Backstrom et al., "Characterization of an internal permissive site in the cholera toxin B-subunit and insertion of epitopes from human immunodeficiency virus-1, hepatitis B virus and enterotoxigenic *Escherichia coli*", Gene. Nov. 20, 1995;165(2):163-71.

Bergamini et al., "Adriamycin selectively inhibits HIV replication in resting macrophages", Int Conf AIDS. Jun 16-21, 1991; 7:109 (Abstract No. W.A.1071).

Berry et al., "Structure of an anti-HIV monoclonal Fab antibody fragment specific to a gp120 C-4 region peptide", Proteins. Nov 15, 2001;45(3):281-2.

Broliden et al., "A monoclonal antibody to human immunodeficiency virus type 1 which mediates cellular cytotoxicity and neutralization", J Virol. Feb. 1990;64(2):936-40.

Bryson et al., "Cross-neutralizing human monoclonal anti-HIV-1 Antibody 2F5: preparation and crystallographic analysis of the free and epitope-complexed forms of its Fab' fragment", Protein and Peptide Letters, vol. 8, No. 5, pp. 413-418, 2001; Bentham Science Publishers Ltd.

Heath et al., "Aggresomes resemble sites specialized for virus assembly", J Cell Biol. Apr. 30, 2001;153(3):449-55.

Johansson et al., "Elimination of HIV-1 infection by treatment with a doxorubicin-conjugated anti-envelope antibody", AIDS. Oct. 3, 2006;20(15):1911-5.

Johnston et al., "Aggresomes: a cellular response to misfolded proteins", J Cell Biol. Dec. 28, 1998;143(7):1883-98.

Paulik et al., "Drug-antibody conjugates with anti-HIV activity", Biochem Pharmacol. Dec. 1, 1999;58(11):1781-90.

Prlic et al., "Immunology. An antibody paradox, resolved.", Science. Mar. 31, 2006;311(5769):1875-6.

Sato et al., "Intergration of cell experiment system", KAST Annual Research Report, 2003 (Abstract).

Schonning et al., "Rapid selection for an N-linked oligosaccharide by monoclonal antibodies directed against the V3 loop of human immunodeficiency virus type 1", J Gen Virol. Apr. 1996;77 ( Pt 4):753-8.

Wileman et al., "Aggresomes and autophagy generate sites for virus replication", Science. May 12, 2002;312 (5775):875-8.

* cited by examiner

*Primary Examiner* — Nicole Kinsey White
(74) *Attorney, Agent, or Firm* — Richard A. Nakashima

(57) ABSTRACT

The present invention concerns methods and compositions for treatment of HIV infection in a subject. The compositions may comprise a targeting molecule against an HIV antigen, such as an anti-HIV antibody or antibody fragment. The anti-HIV antibody or fragment may be conjugated to a variety of cytotoxic agents, such as doxorubicin. In a preferred embodiment, the antibody or fragment is P4/D10. Other embodiments may concern methods of imaging, detection or diagnosis of HIV infection in a subject using an anti-HIV antibody or fragment conjugated to a diagnostic agent. In alternative embodiments, a bispecific antibody with at least one binding site for an HIV antigen and at least one binding site for a carrier molecule may be administered, optionally followed by a clearing agent, followed by administration of a carrier molecule conjugated to a therapeutic agent.

25 Claims, 2 Drawing Sheets

(A)

(B)

METHODS AND COMPOSITIONS FOR TREATMENT OF HUMAN IMMUNODEFICIENCY VIRUS INFECTION WITH CONJUGATED ANTIBODIES OR ANTIBODY FRAGMENTS

RELATED APPLICATIONS

This is a divisional of U.S. application Ser. No. 11/745,692 (now issued U.S. Pat. No. 8,333,971), filed May 8, 2007, which claims the benefit under 35 C.F.R. §119(e) to provisional application Ser. No. 60/800,342, filed May 15, 2006, the entire contents of which are incorporated herein by reference.

BACKGROUND

1. Field of the Invention

The present invention concerns methods and compositions for treating and in preferred embodiments eliminating human immunodeficiency virus (HIV) in infected subjects. In particular embodiments, the compositions and methods concern targeting molecules, such as antibodies or antibody fragments against HIV antigens, for example against HIV envelope antigen. In more particular embodiments, the antibodies or antibody fragments may be conjugated to one or more agents, such as therapeutic agents, diagnostic agents, virostatic agents and/or cytotoxic agents, including but not limited to chemotherapeutic agents such as doxorubicin. In alternative embodiments, bispecific or multispecific antibodies or fragments thereof may be used, with one or more binding sites directed towards HIV antigen(s) and one or more binding sites with affinity for a carrier molecule to which cytotoxic, virostatic or other therapeutic and/or diagnostic agents may be attached.

2. Description of Related Art

Despite encouraging advances in the treatment of human immunodeficiency virus-1 (HIV-1) with anti-retroviral therapy (ART), analyses of peripheral blood and lymph nodes have documented the presence of persistent reservoirs of resting T cells which harbor latent provirus that can activate spontaneously even years after the termination of therapy (Berger et al., *Proc Natl Acad Sci USA* 1998, 95:11511-11513; Blankson et al., *Annu Rev Med* 2002, 53:557-593).

Binding and neutralizing antibodies can prevent attachment of free virus to the cellular receptor, they can bind to the viral surface, and they can induce complement-mediated virolysis of free virions (Parren et al., *AIDS* 1999, 13[Suppl A]:S137-162). Antibodies may also mediate killing of infected cells by antibody-dependent cellular cytotoxicity (ADCC), by coupling NK-cells to infected target cells (Broliden et al., *J Virol* 1990, 64:936-940). However, the use of anti-viral antibodies alone as part of an immunotherapy of patients infected with HIV has not fulfilled its initial promise (Hinkula et al., *J Acquir Immune Defic Syndr* 1994, 7:940-951; Trkola et al., *Nat Med* 2005, 11:615-622).

Attempts have been made to use various viral or cellular components as targets for antibody delivery of therapeutic agents to HIV-infected cells (Davey et al., *J Infect Dis* 1994, 170:1180-1188; Pincus et al., *J Immunol* 2003, 170:2236-2241; Ramachandran et al., *J Infect Dis* 1994, 170:1009-1013; Saavedra-Lozano et al., *Proc Natl Acad Sci USA* 2004, 101:2494-2499). Similar immunotoxins have proved promising in cancer patients (Wu and Senter, *Nat Biotechnol* 2005, 23:1137-1146). However, a need exists for more effective methods and compositions for treatment of HIV-infected cells.

SUMMARY OF THE INVENTION

The present invention fulfills an unresolved need in the art by providing methods and compositions for inhibiting, suppressing, detecting, identifying, localizing and/or eliminating HIV-infected cells. In certain embodiments, the compositions and/or methods may concern targeting molecules against HIV antigens. Such targeting molecules may include, but are not limited to, peptides, antibodies, humanized antibodies, chimeric antibodies, human antibodies or fragments of any such antibodies, and/or antibody analogs. In certain embodiments, the targeting molecules may be unconjugated, for example "naked" antibodies or antibody fragments. In other embodiments, the targeting molecules may be conjugated to one or more therapeutic and/or diagnostic agents. Such agents may include, but are not limited to, a drug, prodrug, virostatic agent, toxin, enzyme, oligonucleotide, radioisotope, radionuclide, immunomodulator, cytokine, label, fluorescent label, luminescent label, paramagnetic label, MRI label, micelle, liposome, nanoparticle, or combination thereof. In particular embodiments, conjugated anti-HIV antibodies or fragments may be administered in vivo to patients with a known or suspected HIV infection. Such administration may block or prevent infection of patient cells with HIV, may reduce or eliminate HIV-infected cells in the patient, and/or may reduce or eliminate residual foci of HIV-infected cells in patients treated previously and/or simultaneously with other known anti-retroviral therapies.

Other embodiments concern methods and/or compositions for treating subjects, such as subjects infected with HIV, SW, other retroviruses. Subjects may include, but are not limited to, humans, animals, cats, dogs, cows, sheep, goats, horses, and mammals. The methods and compositions may comprise one or more naked or conjugated targeting molecules to be administered to a subject. In preferred embodiments, the targeting molecules are antibodies or antibody fragments, including any variation of chimeric, humanized or human antibodies or fragments. Administration may be by any route known in the art, such as oral, nasal, buccal, inhalational, rectal, vaginal or topical. Alternatively, administration may be by orthotopic, intradermal, subcutaneous, intramuscular, intraperitoneal, intraarterial, intrathecal or intravenous injection.

The skilled artisan will realize that one or more HIV targeting molecules, either conjugated or unconjugated, may be administered alone or alternatively in conjunction with other known therapeutic treatments for HIV infection, such as azidothymidine, other nucleoside/nucleotide reverse transcriptase inhibitors, non-nucleoside reverse transcriptase inhibitors, HIV protease inhibitors and/or fusion inhibitors. In certain embodiments, the conjugated HIV targeting molecules may be used in combination with HAART (highly active anti-retroviral therapy). Many anti-HIV therapeutic agents are known in the art and any such known agent may be used, including but not limited to efavirenz, zidovudine, tenofovir, lamivudine, emtricitabine, didanosine, abacavir, stavudine, nevirapine, lopinavir, ritonavir, atazanavir, fosamprenavir, indinavir, nelfinavir, saquinavir, alone or in any combination.

In some embodiments, anti-HIV antibodies or fragments may be administered as part of a bispecific or multispecific antibody complex, with at least one binding site for the HIV antigen and a second binding site for a second target, such as a hapten or carrier molecule. In other embodiments, anti-HIV antibodies or fragments may be covalently attached to or provided as a fusion protein with an antibody, antibody fragment, monoclonal antibody, Fc fragment, Fc-binding protein or antibody binding protein.

In various embodiments, anti-HIV antibodies or fragments may be covalently or non-covalently attached to various moieties by methods well known in the art, such as the use of covalent cross-linking reagents. Many such agents, such as carbodiimides, bisimidates, N-hydroxysuccinimide ester of suberic acid, dimethyl-3,3'-dithio-bispropionimidate, azidoglyoxal, 1,5-difluoro-2,4-(dinitrobenzene) and other cross-linkers of use for proteins and/or peptides are known and may be used.

In other embodiments, the anti-HIV antibodies or fragments may be used as adjuncts for diagnosis and/or imaging purposes. For example, anti-HIV antibodies or fragments may be tagged with any known contrast or detection agent or may be detected using any known methodologies, such as ELISA, etc. The anti-HIV antibodies or fragments may be used ex vivo, for example by immunohistochemistry of tissue sections, to detect residual HIV infection. Alternatively, anti-HIV antibodies or fragments may be administered to a subject for in vivo detection of tissues infected with HIV. Such compositions and methods may be used to detect and/or diagnose the presence of HIV infection, to monitor for residual HIV infection after therapy, and/or to monitor the effectiveness of anti-HIV therapy.

BRIEF DESCRIPTION OF THE DRAWINGS

The following drawings form part of the present specification and are included to further demonstrate certain aspects of particular embodiments of the invention. The embodiments may be better understood by reference to one or more of these drawings in combination with the detailed description presented herein.

DESCRIPTION OF ILLUSTRATIVE EMBODIMENTS

Figure 1:
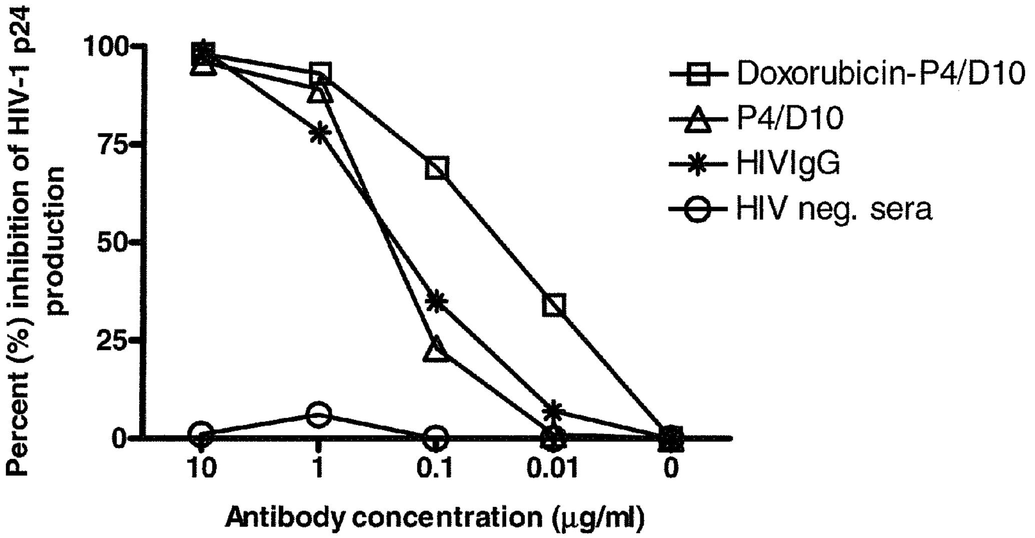
FIG. 1A. HIV-$1_{IIIB}$ neutralization of HIV infection in vitro. The neutralizing capacities of the immunoglobulins were tested by incubating different concentrations of the immunoglobulins with HIV-$1_{IIIB}$ and then assaying the viral infection of HIV susceptible Jurkat T-cells. Both 10 μg/ml doxorubicin-P4/D10 and unlabelled P4/D10 neutralized HIV-$1_{IIIB}$ significantly better than HIV negative sera (p=0.001).
FIG. 1B. HIV-$1_{IIIB}$ inhibition of intercellular spread of HIV infection in vitro. To test whether the immunoglobulins could limit the intercellular spread of HIV-1 infection Jurkat T-cells were mixed in the proportions 0.2%, 1%, 3%, and 5% infected and 99.8%, 99%, 97%, and 95% uninfected cells. The HIV-1 p24 production after treating 3% Jurkat T-cells infected with HIV-$1_{IIIB}$ and 97% uninfected cells with different concentrations of immunoglobulins is shown. The results are shown as percent inhibition of p24 production after 7 days in culture. Doxorubicin-P4/D10 had a significantly better inhibiting effect on production of HIV-1 p24 compared to unlabelled P4/D10, control antibody doxorubicin-LL1, free doxorubicin and HIV-negative serum at a concentration of 0.5 or 0.05 μg/ml (p=0.002).
Figure 1:
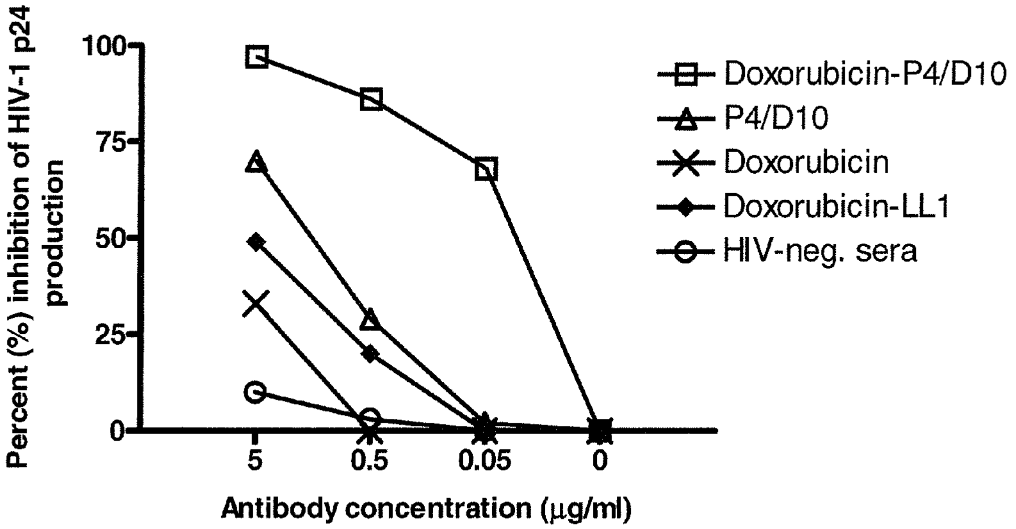

All documents, or portions of documents, cited in this application, including but not limited to patents, patent applications, articles, books, and treatises, are hereby expressly incorporated by reference in their entirety.

DEFINITIONS

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would be mean any number between 90 and 110.

An "antibody", as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion or analog of an immunoglobulin molecule, like an antibody fragment.

An "antibody fragment" is a portion of an antibody such as $F(ab)_2$, $F(ab')_2$, Fab, Fv, sFv, and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition (CDR) units consisting of the amino acid residues that mimic the hypervariable region.

A "therapeutic agent" is an atom, molecule, or compound that is useful in the treatment of a disease. Examples of therapeutic agents include antibodies, antibody fragments, drugs, virostatic agents, toxins, enzymes, nucleases, hormones, immunomodulators, antisense oligonucleotides, small interfering RNA (siRNA), chelators, boron compounds, photoactive agents, dyes, and radioisotopes. Other exemplary therapeutic agents and methods of use are disclosed in U.S. Patent Application Publication Nos. 20050002945, 20040018557, 20030148409 and 20050014207, each incorporated herein by reference.

A "neutralizing antibody" or "neutralizing antibody fragment" is used herein to refer to an antibody or fragment that reacts with an infectious agent (such as a virus) and destroys or inhibits its infectivity and/or virulence.

A "diagnostic agent" is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An "immunoconjugate" is a conjugate of a binding molecule (e.g., an antibody component) with an atom, molecule, or a higher-ordered structure (e.g., with a carrier, a therapeutic agent, or a diagnostic agent).

A "naked antibody" is an antibody that is not conjugated to any other agent.

A "carrier" is an atom, molecule, or higher-ordered structure that is capable of associating with a therapeutic or diagnostic agent to facilitate delivery of such agent to a targeted cell. Carriers may include lipids (e.g., amphiphilic lipids that are capable of forming higher-ordered structures), polysaccharides (such as dextran), proteins, peptides, peptide analogs, peptide derivatives or other higher-ordered structures, such as micelles, liposomes, or nanoparticles. In certain embodiments, a carrier may be designed to be resistant to proteolytic or other enzymatic degradation, for example by substituting D-amino acids for naturally occurring L-amino acids in a protein or peptide.

As used herein, the term "antibody fusion protein" refers to a recombinantly produced antigen-binding molecule in which two or more of the same or different scFv or antibody fragments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds to one such epitope, for example a diabody with two binding site reactive with the same antigen. The fusion protein may comprise a single antibody component, a multivalent or multispecific combination of different antibody components, or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A "bispecific antibody" is an antibody that can bind simultaneously to two targets of different structure. Bispecific antibodies and bispecific antibody fragments that are of particular interest have at least one arm that specifically binds to, for example, an HIV envelope protein and at least one other arm that specifically binds to a targetable conjugate that bears a therapeutic or diagnostic agent.

An antibody or immunoconjugate preparation, or a composition described herein, is said to be administered in a "therapeutically effective amount" if the amount administered is physiologically significant. An agent is physiologically significant if its presence results in a detectable change in the physiology of a recipient mammal. In particular, an anti-HIV antibody preparation is physiologically significant if its presence reduces, inhibits or eliminates HIV-infected cells or reduces, inhibits or eliminates HIV infection of non-infected cells.

A composition is said to be a "pharmaceutically acceptable carrier" if its administration can be tolerated by a recipient patient. Sterile phosphate-buffered saline is one example of a pharmaceutically acceptable carrier. Other suitable carriers are well known to those in the art. See, for example, REMINGTON'S PHARMACEUTICAL SCIENCES, 19th Ed. (Mack Publishing Co. 1995), and Goodman and Gilman's THE PHARMACOLOGICAL BASIS OF THERAPEUTICS (Goodman et al., Eds. Macmillan Publishing Co., New York, 1980 and 2001 editions).

Abbreviations used are:

ABS, sodium acetate buffer containing 150 mM sodium chloride;

ADCC, antibody-dependent cellular cytotoxicity;

DTT, dithiothreitol;

ELISA, enzyme-linked immunosorbent assay;

ART, anti-retroviral therapy;

HIV, human immunodeficiency virus;

Mab, monoclonal antibody;

MuLV, Murine Leukemia Virus;

PBMC, peripheral blood mononuclear cells;

$TCID_{50}$, 50% tissue culture infectious dose.

Antibodies

Various embodiments may concern antibody ligands against one or more antigens or epitopes of HIV. In preferred embodiments, the antigen or epitope is one that is exposed on the surface of HIV-infected cells, such as the HIV envelope protein. Techniques for preparing and using various antibody-based constructs and fragments are well known in the art. Means for preparing and characterizing antibodies are also well known in the art (See, e.g., Harlowe and Lane, 1988, *Antibodies: A Laboratory Manual*, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.).

Monoclonal Antibodies

While preferred embodiments may concern the use of the P4/D10 antibody, other anti-HIV antibodies may be obtained, prepared and/or used. A variety of antibodies against HIV have been reported and in certain embodiments any such known anti-HIV antibody may be utilized. For example, 4E10 (Rosa et al., Immunity 2:163-73, 2005); 2F5 (Bryson et al., Protein and Peptide Letters, 8:413-18, 2001); 3D6 (Ruker et al., Ann. NY Acad. Sci. 646:212-19, 1991); C37 (Cao et al., DNA and Cell Biology, 12:836-41, 2004); LACY, 1F58, 1GGGC (Berry et al., Proteins, 45:281-82, 2001); 2G12 (Armbruster et al., J. Antimicrob. Chemother. 54:915-20, 2004), each incorporated herein by reference. In alternative embodiments, monoclonal antibodies may be readily prepared through use of well-known techniques, such as those exemplified in U.S. Pat. No. 4,196,265. Typically, this technique involves immunizing a suitable animal with a selected immunogen composition. Cells from rodents such as mice and rats are preferred. Mice are more preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the Mab generating protocol. These cells may be obtained from biopsied spleens, tonsils or lymph nodes, or from a peripheral blood sample. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B-lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art. For example, where the immunized animal is a mouse, one may use P3-X63/Ag8, P3-X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus, and those using polyethylene glycol (PEG), such as 37% (v/v) PEG, have been described. The use of electrically induced fusion methods is also appropriate.

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two wk. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide Mabs. The cell lines may be exploited for Mab production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide Mabs in high concentration. The individual cell lines also could be cultured in vitro, where the Mabs are naturally secreted into the culture medium from which they can be readily obtained in high concentrations. Mabs produced by either means may be further purified, if desired, using filtration, centrifugation, and various chromatographic methods such as HPLC or affinity chromatography.

Production of Antibody Fragments

Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide a 5S fragment denoted $F(ab')_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotide linker sequence. The structural gene is inserted into an expression vector that is subsequently introduced into a host cell, such as *E. coli*. The recombinant host cells synthesize a single polypeptide chain with a linker peptide bridging the two V domains. Methods for producing sFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Chimeric and Humanized Antibodies

A chimeric antibody is a recombinant protein in which the variable regions of, for example, a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

Human Antibodies

In another embodiment, an antibody may be a human monoclonal antibody. Such antibodies may be obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994).

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as HIV infection or AIDS. The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, such as biopanning. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. A non-limiting example of such a system is the XENOMOUSE® (e.g., Green et al., 1999, *J. Immunol. Methods* 231:11-23) from Abgenix (Fremont, Calif.). In the XENOMOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Neutralizing Antibodies

In certain embodiments, neutralizing antibodies or fragments thereof that are capable of destroying or inhibiting the infectivity and/or virulence of HIV are preferred. A variety of HIV neutralizing antibodies are known in the art and any such known antibodies or fragments thereof may be used, including but not limited to P4/D10, 2G12 (e.g., Joos et al., *Antimicrob Agents Chemother* 2006, 50:1773-79), 4E10 (Joos et al., 2006), 2F5 (Joos et al., 2006), b12 (e.g., Wu et al., *J Virol* 2006, 80:2585), X5 (Moulard et al., *Proc Natl Acad Sci* 2002, 99:6913-18) or any combination thereof. Where multispecific antibodies or fragments are used, the skilled artisan will realize that multiple antibodies or fragments that bind to the same or different HIV epitopes may be combined. Although antibodies against the HIV envelope protein (gp120) and/or gp41 are preferred, the skilled artisan will realize that other HIV target antigens may be utilized to develop antibodies or fragments thereof that will target HIV-infected cells. In some cases, antibodies or fragments that bind to one or more HIV antigens in combination with T-cell antigens (e.g., CD4, CCR5 and/or CXCR4) may be utilized.

Fusion Proteins

Various embodiments may concern fusion proteins. These molecules generally have all or a substantial portion of a peptide, linked at the N- or C-terminus, to all or a portion of a second polypeptide or protein. For example, fusions may employ leader sequences from other species to permit the recombinant expression of a protein in a heterologous host. Another useful fusion includes the attachment of an immunologically active domain, such as an antibody or fragment, to a therapeutic agent, such as a peptide or protein toxin or enzyme. Yet another useful form of fusion may include attachment of a moiety of use for purification, such as the FLAG epitope (Prickett et al., 1989, *Biotechniques* 7:580-589; Castrucci et al., 1992, *J Virol* 66:4647-4653). Methods of generating fusion proteins are well known to those of skill in the art. Such proteins may be produced, for example, by chemical attachment using bifunctional cross-linking reagents, by de novo synthesis of the complete fusion protein, or by attachment of a DNA sequence encoding a first protein or peptide to a DNA sequence encoding a second peptide or protein, followed by expression of the intact fusion protein.

Bispecific Antibodies

In certain embodiments, bispecific or multispecific antibodies or fragments may be utilized. Such antibodies or fragments will comprise at least one binding site for an HIV-associated antigen and at least one other binding site, for example against a carrier molecule conjugated to therapeutic and/or diagnostic agents, a cytokine, a cell surface receptor or other antigen.

In general, discrete $Y_R$ and $V_L$ domains of antibodies produced by recombinant DNA technology may pair with each other to form a dimer (recombinant Fv fragment) with binding capability (U.S. Pat. No. 4,642,334). However, such non-covalently associated molecules are not sufficiently stable under physiological conditions to have any practical use. Cognate $Y_R$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405. Reduction of the peptide linker length to less than 12 amino acid residues prevents pairing of $Y_H$ and $Y_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabodies) and tetramers (termed tetrabodies) are favored, but the exact patterns of oligomerization appear to depend on the composition as well as the orientation of V-domains ($V_H$-linker-$V_L$ or $V_L$-linker-$V_H$), in addition to the linker length.

Monospecific diabodies, triabodies, and tetrabodies with multiple valencies have been obtained using peptide linkers consisting of 5 amino acid residues or less. Bispecific diabodies, which are heterodimers of two different scFvs, each scFv consisting of the $V_H$ domain from one antibody connected by a short peptide linker to the $V_L$ domain of another antibody, have also been made using a dicistronic expression vector that contains in one cistron a recombinant gene construct comprising $V_{H1}$-linker-$V_{L2}$ and in the other cistron a second recombinant gene construct comprising $V_{H2}$-linker-$V_{L1}$ (Holliger, et al. Proc Natl Acad Sci USA. 1993; 90: 6444-6448; Atwell, et al., Mol Immunol. 1996; 33:1301-1302; Holliger, et al. Nature Biotechnol. 1997; 15: 632-631; Helfrich, et al. Int. J Cancer. 1998; 76: 232-239; Kipriyanov, et al. Int J Cancer. 1998; 77: 763-772; Holliger, et al. Cancer Res. 1999; 59: 2909-2916).

More recently, a tetravalent tandem diabody (termed tandab) with dual specificity has also been reported (Cochlovius, et al. Cancer Res. 2000; 60: 4336-4341). The bispecific tandab is a dimer of two identical polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

Methods of manufacturing scFv-based agents of multivalency and multispecificity by varying the linker length were disclosed in U.S. Pat. No. 5,844,094, U.S. Pat. No. 5,837,242, and WO 98/44001. Methods of manufacturing scFv-based agents of multivalency and multispecificity by constructing two polypeptide chains, one comprising of the $V_H$ domains from at least two antibodies and the other the corresponding $V_L$ domains were disclosed in U.S. Pat. No. 5,989,830 and U.S. Pat. No. 6,239,259. A recombinantly produced bispecific or trispecific antibody in which the c-termini of CH1 and $C_L$ of a Fab are each fused to a scFv derived from the same or different monoclonal antibodies was disclosed in U.S. Pat. No. 6,809,185.

Methods for construction and use of bispecific and multispecific antibodies are disclosed, for example, in U.S. Patent Application Publication No. 20050002945, filed Feb. 11, 2004, the entire text of which is incorporated herein by reference. A variety of recombinant methods can be used to produce bispecific antibodies and antibody fragments. For example, bispecific antibodies and antibody fragments can be produced in the milk of transgenic livestock. (See, e.g., Colman, A., Biochem. Soc. Symp., 63: 141-147, 1998; U.S. Pat. No. 5,827,690, each incorporated herein by reference.) Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow alpha-lactoglobulin gene, the sheep beta-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

Pre-Targeting

One strategy for use of bispecific antibodies includes pre-targeting methodologies, in which an effector molecule is administered to a subject after a bispecific antibody has been administered. The bispecific antibody, which would include a binding site for an HIV antigen and one for a carrier conjugated to one or more effector molecules, localizes to the diseased tissue and increases the specificity of localization of the effector to the diseased tissue (U.S. Patent Application No. 20050002945). Because the effector molecule may be cleared from circulation much more rapidly than the bispecific antibody, normal tissues may have a decreased exposure to the effector molecule when a pretargeting strategy is used than when the effector molecule is directly linked to the disease targeting antibody.

Pretargeting methods have been developed to increase the target:background ratios of detection or therapeutic agents. Examples of pre-targeting and biotin/avidin approaches are described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. No. 6,077,499; U.S. Ser. No. 09/597,580; U.S. Ser. No. 10/361,026; U.S. Ser. No. 09/337,756; U.S. Ser. No. 09/823,746; U.S. Ser. No. 10/116,116; U.S. Ser. No. 09/382,186; U.S. Ser. No. 10/150,654; U.S. Pat. No. 6,090,381; U.S. Pat. No. 6,472,511; U.S. Ser. No. 10/114,315; U.S. Provisional Application No. 60/386,411; U.S. Provisional Application No. 60/345,641; U.S. Provisional Application No. 60/3328,835; U.S. Provisional Application No. 60/426,379; U.S. Ser. No. 09/823,746; U.S. Ser. No. 09/337,756; and U.S. Provisional Application No. 60/342,103, all of which are incorporated herein by reference.

In certain embodiments, bispecific antibodies and targetable constructs may be of use in treating and/or imaging diseased tissues, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2001.

Dock and Lock (DNL)

In certain embodiments, bispecific antibodies or fragments, or conjugates of antibodies or fragments, may be assembled using a technology known as dock and lock (DNL). Further details of DNL technology may be found in U.S. patent application Ser. No. 11/389,358, filed Mar. 24, 2005; Ser. No. 11/391,584, filed Mar. 28, 2006; Ser. No. 11/478,021, filed Jun. 29, 2006; Ser. No. 11/633,729, filed Jun. 21, 2007; and U.S. Provisional Patent Application Ser. No. 60/864,530, filed Nov. 6, 2006, the text of each of which is incorporated herein by reference in its entirety.

To summarize, DNL technology involves targeting binding between two or more complementary sequences, such as a dimerization and docking domain (DDD) of, for example, the regulatory subunits of c-AMP-dependent protein kinas A, and the anchoring domain found in various A-kinase anchoring proteins (AKAPs) that mediates association with the R subunits of PKA. However, the skilled artisan will realize that other dimerization and docking domains and anchoring domains are known and any such known domains may be used within the scope of the claimed subject matter. Other exemplary 4-helix bundle type DDD domains may be obtained from p53, DCoH (pterin 4 alpha carbinolamine dehydratase/dimerization cofactor of hepatocyte nuclear factor 1 alpha (TCF1)) and HNF-1 (hepatocyte nuclear factor 1). Other AD sequences of potential use may be found in Patent Application Serial No. US20003/0232420A1, the entire text of which is incorporated herein by reference.

These complementary binding pairs may be covalently attached to various functional units, such as antibodies or antibody fragments, or therapeutic or diagnostic agents, forming therapeutic or diagnostic complexes of determined specificity and activity. The skilled artisan will realize that there are a multiplicity of ways in which such complexes could be formed, for example by incorporating AD or DDD sequences into fusion proteins comprising a Fab, Fab', IgG, scFc or other antibody or fragment with known binding specificity. For example, a bispecific complex may be formed by incorporating AD and DDD sequences into antibodies or fragments specific for two different target antigens. Alternatively, an antibody or fragment attached to a DDD or AD moiety may be combined with a therapeutic protein or peptide, such as a hormone, enzyme, ribonuclease, onconase or other agent that is attached to a complementary AD or DDD moiety. A number of such potential complexes are described in the patent applications listed above and any of such known complexes may be utilized.

Conjugation of Therapeutic or Diagnostic Agents to anti-HIV Antibodies

In various embodiments, therapeutic agents may be conjugated to anti-HIV antibodies, fragments or other targeting molecules for delivery to HIV infected cells. Therapeutic agents of use may comprise one or more of aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, dactinomycin, daunomycin glucuronide, daunorubicin, doxorubicin, 2-pyrrolinodoxorubicine (2P-DOX), cyano-morpholino doxorubicin, doxorubicin glucuronide, epirubicin glucuronide, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyurea, idarubicin, ifosfamide, L-asparaginase, leucovorin, lomustine, mechlorethamine, melphalan, mercaptopurine, 6-mercaptopurine, methotrexate, mitoxantrone, mithramycin, mitomycin, mitotane, phenyl butyrate, procarbazine, pentostatin, PSI-341, semustine, streptozocin, taxanes, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas* exotoxin,

*Pseudomonas* endotoxin, an antisense oligonucleotide, an interference RNA, or a combination thereof.

Additional moieties can be conjugated to the HIV targeting molecules described herein. For example, drugs, toxins, radioactive compounds, enzymes, hormones, cytotoxic proteins, chelates, cytokines, and other functional agents may be conjugated to the HIV targeting molecules. Conjugation can be via, for example, covalent attachments to amino acid residues containing amine, carboxyl, thiol or hydroxyl groups in their side-chains. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the HIV targeting molecules preferably does not significantly affect the binding activity or specificity compared to the unmodified structures. In addition, cytotoxic and/or virostatic agents may be first coupled to a polymeric carrier, which is then conjugated to a HIV targeting molecule. For this method, see Ryser et al., *Proc. Natl. Acad. Sci. USA,* 75:3867-3870, 1978, U.S. Pat. No. 4,699,784, and U.S. Pat. No. 4,046,722, which are incorporated herein by reference.

The conjugates described herein can be prepared by methods known for linking antibodies with lipids, carbohydrates, proteins, radionuclides, or other atoms and molecules. For example, the HIV targeting molecules described herein can be linked to one or more of the carriers described herein (e.g., lipids, polymers, liposomes, micelles, or nanoparticles) to form a conjugate, which can then incorporate a therapeutic or diagnostic agent either covalently, non-covalently, or otherwise. Alternatively, any of the HIV targeting molecules described herein can be conjugated directly with one or more therapeutic or diagnostic agents described herein.

For example, a HIV targeting molecule can be radiolabeled with $^{131}$I and conjugated to a lipid, such that the resulting conjugate can form a liposome. The liposome may incorporate one or more therapeutic (e.g., a drug such as FUdR-dO) or diagnostic agents. The formation of liposomes and micelles is known in the art. See, e.g., Wrobel and Collins, Biochimica et Biophysica Acta (1995), 1235: 296-304; Lundberg et al., J. Pharm. Pharmacol. (1999), 51:1099-1105; Lundberg et al., Int. J. Pharm. (2000), 205:101-108; Lundberg, J. Pharm. Sci. (1994), 83:72-75; Xu et al., Molec. Cancer Ther. (2002), 1:337-346; Torchilin et al., Proc. Nat'l. Acad. Sci., U.S.A. (2003), 100:6039-6044; U.S. Pat. No. 5,565,215; U.S. Pat. No. 6,379,698; and U.S. 2003/0082154.

Nanoparticles or nanocapsules formed from polymers, silica, or metals, which are useful for drug delivery or imaging, have been described as well. See, e.g., West et al., Applications of Nanotechnology to Biotechnology (2000), 11:215-217; U.S. Pat. No. 5,620,708; U.S. Pat. No. 5,702,727; and U.S. Pat. No. 6,530,944. The conjugation of antibodies or binding molecules to liposomes to form a targeted carrier for therapeutic or diagnostic agents has been described. See, e.g., Bendas, Biodrugs (2001), 15:215-224; Xu et al., Mol. Cancer Ther (2002), 1:337-346; Torchilin et al., Proc. Nat'l. Acad. Sci. U.S.A (2003), 100:6039-6044; Bally, et al., J. Liposome Res. (1998), 8:299-335; Lundberg, Int. J. Pharm. (1994), 109:73-81; Lundberg, J. Pharm. Pharmacol. (1997), 49:16-21; Lundberg, Anti-cancer Drug Design (1998), 13: 453-461. See also U.S. Pat. No. 6,306,393; U.S. Ser. No. 10/350,096; U.S. Ser. No. 09/590,284, and U.S. Ser. No. 60/138,284, filed Jun. 9, 1999. All these references are incorporated herein by reference.

A wide variety of diagnostic and therapeutic agents can be advantageously used to form the conjugates of the HIV targeting molecules, or may be linked to haptens that bind to a recognition site on the HIV targeting molecules. Diagnostic agents may include radioisotopes, enhancing agents for use in MRI or contrast agents for ultrasound imaging, and fluorescent compounds. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509).

In order to load a HIV targeting molecule with radioactive metals or paramagnetic ions, it may be necessary to first react it with a carrier to which multiple copies of a chelating group for binding the radioactive metals or paramagnetic ions have been attached. Such a carrier can be a polylysine, polysaccharide, or a derivatized or derivatizable polymeric substance having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and the like known to be useful for this purpose. Carriers containing chelates are coupled to the HIV targeting molecule using standard chemistries in a way to minimize aggregation and loss of immunoreactivity.

Other, more unusual, methods and reagents that may be applied for preparing such conjugates are disclosed in U.S. Pat. No. 4,824,659, which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV. Some useful diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In. The same chelates complexed with non-radioactive metals, such as manganese, iron and gadolinium, are useful for MRI, when used along with the HIV targeting molecules and carriers described herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and proapoptotic agents, particularly doxorubicin, methotrexate, taxol, CPT-11, camptothecans, and others from these and other classes of cytotoxic agents. Other cytotoxic agents include nitrogen mustards, alkyl sulfonates, nitrosoureas, triazenes, folic acid analogs, pyrimidine analogs, purine analogs, platinum coordination complexes, and the like. Suitable cytotoxic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable cytotoxic agents, such as experimental drugs, are known to those of skill in the art, and may be conjugated to the HIV targeting molecules described herein using methods that are known in the art.

Another class of therapeutic agents consists of radionuclides that emit α-particles (such as $^{212}$Pb, $^{212}$Bi, $^{213}$Bi, $^{211}$At, $^{223}$Ra, $^{225}$Ac, β-particles (such as $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}Lu$, $^{186}Re$, $^{188}Re$, $^{189}Re$), or Auger electrons (such as $^{111}In$, $^{125}I$, $^{67}Ga$, $^{191}Os$, $^{193m}Pt$, $^{195m}Pt$, $^{195m}Hg$). The HIV targeting molecules may be labeled with one or more of the above radionuclides using methods as described for the diagnostic agents.

In certain embodiments, the therapeutic agents of use may comprise one or more aggresome inhibitors. Aggresomes are large intracellular complexes that were thought to form in response to misfolded protein (see, e.g., Heath et al., J. Cell Biol. 153:449-55, 2001; Johnstone et al., J. Cell Biol. 143: 1883-98, 1998; Wileman, Science 312:875-78, 2006). More recently, it has been suggested that aggresomes may function in the assembly of viral particles (Heath et al., 2001; Wileman, 2006). Aggresome inhibitors may therefore function to block or inhibit the formation of new infectious viral particles from cells infected with HIV or other viruses. A variety of aggresome inhibitors are known, such as ALLN, nocodazole, colchicine and vinblastine (Johnston et al., 1998), other microtubule inhibitors (Gerdes and Katsanis, Hum. Molec. Genet. 14:R291-300, 2005); bortezomib (Velcade) (Catley et al., Blood 108:3441-49, 2006), tubacin, histone deacetylase inhibitors (Corcoran et al., Curr. Biol. 14:488-92, 2004), and any such known aggresome inhibitor may be used.

In various embodiments, one or more immunomodulators may be conjugated to an anti-HIV antibody or fragment for administration to a patient, or alternatively may be co-administered to the patient. As used herein, the term "immunomodulator" includes cytokines, stem cell growth factors, lymphotoxins and hematopoietic factors, such as interleukins, colony stimulating factors, interferons (e.g., interferons-α, -β and -γ) and the stem cell growth factor designated "S1 factor." Examples of suitable immunomodulator moieties include IL-2, IL-6, IL-10, IL-12, IL-18, IL-21, interferon-gamma, TNF-alpha, and the like.

The term "cytokine" is a generic term for proteins or peptides released by one cell population which act on another cell as intercellular mediators. As used broadly herein, examples of cytokines include lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to a site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines. Similarly, the terms immunomodulator and cytokine overlap in their respective members.

A suitable peptide containing a detectable label (e.g., a fluorescent molecule), or a virostatic and/or cytotoxic agent, (e.g., a radioiodine), can be covalently, non-covalently, or otherwise associated with the HIV targeting molecules. For example, a therapeutically useful conjugate can be obtained by incorporating a photoactive agent or dye onto the HIV targeting molecules. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Aptamers

In alternative embodiments, the disclosed compositions and methods may utilize alternative forms of binding molecules to antibodies or antibody fragments, such as aptamers. Aptamers are typically synthetic oligonucleotides that can adopt three-dimensional conformations that provide antibody-like binding affinities and specificities for selected target molecules. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)$NR_2$, P(O)R, P(O)OR', CO, or $CNR_2$, wherein R is H or alkyl (1-20C) and R' is alkyl (1-20C); in addition, this group may be attached to adjacent nucleotides through O or S. Not all linkages in an oligomer need to be identical.

Methods for preparation and screening of aptamers that bind to particular targets of interest are well known, for example U.S. Pat. No. 5,475,096 and U.S. Pat. No. 5,270,163, each incorporated by reference. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) is retained during separation. Each cycle results in an enrichment of aptamers with high affinity for the target. Repetition for between three to six selection and amplification cycles may be used to generate aptamers that bind with high affinity and specificity to the target. Aptamers may be conjugated to therapeutic agents by standard nucleic acid labeling techniques well known in the art.

Avimers

In certain embodiments, the disclosed compositions or methods may utilize one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains that may exhibit improved affinity (in some cases sub-nanomolar) and specificity compared with single-epitope binding proteins. (Id.) In various embodiments, avimers may be attached to therapeutic agents for use in the claimed methods and compositions using standard protein cross-linking or labeling techniques discussed herein. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Formulation and Administration

The HIV targeting molecules, including their conjugates, may be further formulated to obtain compositions that include one or more pharmaceutically suitable excipients, one or more additional ingredients, or some combination of these. These can be accomplished by known methods to prepare pharmaceutically useful dosages, whereby the active ingredients (i.e., the HIV targeting molecules or conjugates), are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

One route for administration of the compositions described herein is parenteral injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising HIV targeting molecules can be used for intravenous administration via, for example, bolus injection or continuous infusion. Compositions for injection can be presented in unit dosage form, e.g., in ampules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, tris(hydroxymethyl)aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. Systemic administration of the formulated composition is typically made every two to three days or once a week if a humanized form of the antibody is used as a template for the HIV targeting molecules. Alternatively, daily administration is useful. Usually administration is by either intramuscular injection or intravascular infusion.

The compositions may be administered to a mammal subcutaneously or by other parenteral routes. Moreover, the administration may be by continuous infusion or by single or multiple boluses. Methods useful for the antibodies or immunoconjugates can be applied to the compositions described herein. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of the active ingredient that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

Pharmaceutical methods employed to control the duration of action of immunoconjugates or antibodies may be applied to the formulated compositions described herein. Control release preparations can be achieved through the use of biocompatible polymers to complex or adsorb the immunoconjugate or naked antibody, for example, matrices of poly(ethylene-co-vinyl acetate) and matrices of a polyanhydride copolymer of a stearic acid dimer and sebacic acid. See Sherwood et al., Bio/Technology (1992), 10: 1446. The rate of release of an immunoconjugate or antibody from such a matrix depends upon the molecular weight of the immunoconjugate or antibody, the amount of immunoconjugate, antibody within the matrix, and the size of dispersed particles. See Saltzman et al., Biophys. J (1989), 55: 163; Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

For purposes of therapy, the composition is administered to a mammal in a therapeutically effective amount. A suitable subject for the therapeutic and diagnostic methods disclosed herein is usually a human, although a non-human animal subject is also contemplated.

The compositions may be administered by aerosol to achieve localized delivery to the lungs. Either an aqueous aerosol or a nonaqueous (e.g., fluorocarbon propellent) suspension could be used. Sonic nebulizers preferably are used in preparing aerosols to minimize exposing the HIV targeting molecule in the compositions to shear, which can result in its degradation and loss of activity.

A HIV targeting molecule linked to a radionuclide may be effective for therapy. After it has been determined that the HIV targeting molecule is localized at one or more infectious sites in a subject, higher doses of the labeled composition, generally from 20 mCi to 150 mCi per dose for $^{131}$I, 5 mCi to 30 mCi per dose for $^{90}$Y, or 5 mCi to 20 mCi per dose of $^{186}$Re, each based on a 70 kg patient weight, are injected. Injection may be intravenous, intraarterial, intralymphatic, intrathecal, or intracavitary (i.e., parenterally), and may be repeated. It may be advantageous for some therapies to administer multiple, divided doses, thus providing higher toxic doses without usually effecting a proportional increase in radiation of normal tissues.

In still other embodiments, anti-HIV antibodies or fragments may be modified for oral or inhalational administration by conjugation to certain proteins, such as the Fc region of IgG1 (see Examples 3-7). Methods for preparation and use of peptide-Fc conjugates are disclosed, for example, in Low et al. (2005, *Hum. Reprod.* 20:1805-13) and Dumont et al. (2005, *J. Aerosol. Med.* 18:294-303), each incorporated herein by reference. Low et al. (2005) disclose the conjugation of the alpha and beta subunits of FSH to the Fc region of IgG1 in single chain or heterodimer form, using recombinant expression in CHO cells. The Fc conjugated peptides were absorbed through epithelial cells in the lung or intestine by the neonatal Fc receptor mediated transport system. The Fc conjugated peptides exhibited improved stability and absorption in vivo compared to the native peptides. It was also observed that the heterodimer conjugate was more active than the single chain form. Larger proteins, such as erythropoietin, may also be effectively delivered by inhalation using Fc conjugation (Dumont et al., 2005).

Uses for Treatment and Diagnosis: Applications Not Involving Pretargeting

The use of radioactive and non-radioactive diagnostic agents, which are linked to the HIV targeting molecules, is contemplated. Suitable non-radioactive diagnostic agents are those used for magnetic resonance imaging (MRI), computed tomography (CT) or ultrasound. MRI agents include, for example, non-radioactive metals, such as manganese, iron and gadolinium, which are complexed with suitable chelates such as 2-benzyl-DTPA and its monomethyl and cyclohexyl analogs. See U.S. Ser. No. 09/921,290 filed on Oct. 10, 2001, which is incorporated in its entirety by reference.

The HIV targeting molecules may be labeled with a radioisotope useful for diagnostic imaging. Suitable radioisotopes may include those in the energy range of 60 to 4,000 KeV, or more specifically, $^{18}$F, $^{52}$Fe, $^{62}$Cu, $^{64}$Cu, $^{67}$Cu, $^{67}$Ga, $^{68}$Ga, $^{86}$Y, $^{89}$Zr $^{94m}$Tc, $^{94}$Tc, $^{99m}$Tc, $^{45}$Ti, $^{111}$In, $^{123}$I, $^{124}$I, $^{125}$I, $^{131}$I, $^{154\text{-}158}$Gd, $^{177}$Lu, $^{32}$P, $^{188}$Re, and the like, or a combination thereof. See, e.g., U.S. Patent Application entitled "Labeling Targeting Agents with Gallium-68"—Inventors G. L. Griffiths and W. J. McBride, and U.S. Provisional Application No. 60/342,104, which discloses positron emitters, such as $^{18}$F, $^{68}$Ga, $^{94m}$Tc, and the like, for imaging purposes; (incorporated herein by reference). Detection can be achieved, for example, by single photon emission computed tomography (SPECT), or positron emission tomography (PET).

In another embodiment the HIV targeting molecules may be labeled with one or more radioactive isotopes useful for killing HIV-infected cells, which include β-emitters (such as $^{32}$P, $^{33}$P, $^{47}$S, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}$Lu, $^{186}$Re, $^{188}$Re, $^{189}$Re), Auger electron emitters (such as $^{111}$In, $^{125}$I, $^{67}$Ga, $^{191}$Os, $^{193m}$Pt, $^{195}$Pt, $^{195m}$Hg, α-emitters (such as $^{212}$Pb, $^{212}$Bi, $^{213}$Bi, $^{211}$At, $^{223}$Ra, $^{225}$Ac), or a combination thereof.

The HIV targeting molecules may be used for MRI by linking to one or more image enhancing agents, which may include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). Similarly, the HIV targeting molecules may be used for ultrasound imaging by linking to one or more image enhancing agents currently on the market. U.S. Pat. No. 6,331,175 describes MRI technique and the preparation of antibodies conjugated to an MRI enhancing agent and is incorporated in its entirety by reference.

A functional protein, such as a toxin, may be present in the HIV targeting molecules in several ways. For example, a functional protein may be directly attached to an anti-HIV antibody or fragment as a fusion protein, using standard molecular biology techniques. Alternatively functional proteins may be covalently conjugated to anti-HIV antibodies or fragments by known chemical cross-linking methods. Toxins that may be used in this regard include ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. (See, e.g., Pastan et al., Cell (1986), 47:641; Goldenberg, C A—A Cancer Journal for Clinicians (1994), 44:43; Sharkey and Goldenberg, C A Cancer J. Clin. 56:226 (2006), each incorporated herein by reference.) Additional toxins suitable for use herein are known to those of skill in the art and are disclosed in U.S. Pat. No. 6,077,499, which is incorporated in its entirety by reference. Other functional proteins of interest include various cytokines, enzymes, and fluorescent proteins.

Uses for Treatment and Diagnosis: Applications Involving Pretargeting

Pretargeting is a multistep process originally developed to resolve the slow blood clearance of directly targeting antibodies, which contributes to undesirable toxicity to normal tissues, in particular, bone marrow. With pretargeting, a radionuclide or other therapeutic agent is attached to a small compound that is cleared within minutes from the blood. The pretargeting agent, which is capable of recognizing the small radiolabeled compound in addition to the target antigen, is administered first, and the radiolabeled compound is administered at a later time when the pretargeting agent is sufficiently cleared from the blood.

A pretargeting method of treating or diagnosing a disease or disorder in a subject is provided by: (1) administering to the subject a bispecific HIV-targeting molecule as described above, where at least one antigen binding site is directed against an HIV marker, and the other antigen binding site is directed to a targetable construct containing a bivalent hapten; (2) optionally administering to the subject a clearing composition, and allowing the composition to clear the binding structure from circulation; and (3) administering to the subject the targetable construct containing a bivalent hapten, where the targetable construct further contains one or more chelated or chemically bound therapeutic or diagnostic agents. A variety of clearing agents and methods are known in the art and may be used for pretargeting, such as anti-idiotypic antibodies that complex with an HIV-targeting antibody or attachment of tags or labels (e.g., monosaccharides) to an HIV-targeting antibody that may be complexed with other agents (such as a monosaccharide-binding antibody). Use of avidin-biotin binding interactions for clearing methods are also known in the art.

Also provided is a method of antibody dependent enzyme prodrug therapy (ADEPT) by (1) administering to a patient an HIV targeting molecule as above, where the structure contains a covalently attached enzyme capable of activating a prodrug, (2) optionally administering to the subject a clearing composition, and allowing the composition to clear the binding structure from circulation, and (3) administering the prodrug to the patient.

IMP 411 Targetable Construct

In preferred embodiments, a targetable construct may comprise one or more histamine-succinyl-glycine (HSG) moieties and an antigen-binding site may be associated with an HSG-binding antibody or fragment, such as the 679 antibody or fragment. (see, e.g., U.S. Pat. No. 6,962,702, incorporated herein by reference). The targetable construct may be conjugated to any known diagnostic and/or therapeutic agent, using known pretargeting techniques (e.g., U.S. Pat. No. 6,962,702). An exemplary targetable construct, known as IMP 411, that comprises two HSG moieties has the formula DOTA-D-Cys(3-SP-Gly-20-O-SN38)-D-Ala-D-Lys(HSG)-D-Tyr-D-Lys(HSG)-$NH_2$. IMP 411 may be linked, for example, to SN38 chemotherapeutic agents, as indicated in the formula above. Alternatively, other therapeutic or diagnostic agents may be incorporated into or conjugated to the same peptide backbone.

Additional Uses

In certain embodiments, HIV targeting molecules may be of use in treating and/or imaging HIV-infected tissues, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2001. Such imaging can be conducted by direct labeling of the HIV targeting molecule, or by a pretargeted imaging method, as described in Goldenberg et al, "Antibody Pretargeting Advances Cancer Radioimmunodetection and Radiotherapy," (J. Clin. Oncol., 2006 24:823-34), see also U.S. Patent Publication Nos. 20050002945, 20040018557, 20030148409 and 20050014207, each incorporated herein by reference.

In some embodiments, the HIV targeting molecules disclosed and claimed herein may be of use in radionuclide therapy or radioimmunotherapy methods (see, e.g., Govindan et al., 2005, Technology in Cancer Research & Treatment, 4:375-91; Sharkey and Goldenberg, 2005, J. Nucl. Med. 46:115S-127S; Goldenberg et al., 2006, J. Clin. Oncol. 24:823-34, each incorporated herein by reference.)

In another embodiment, a radiosensitizer can be used in combination with a naked or conjugated HIV targeting molecule, antibody or antibody fragment. For example, the radiosensitizer can be used in combination with a radiolabeled HIV targeting molecule. The addition of the radiosensitizer can result in enhanced efficacy when compared to treatment with the radiolabeled HIV targeting molecule alone. Radiosensitizers are described in D. M. Goldenberg (ed.), CANCER THERAPY WITH RADIOLABELED ANTIBODIES, CRC Press (1995), which is incorporated herein by reference.

The HIV targeting molecule, for use in any of the claimed methods, may be associated or administered with cytokines and immune modulators. These cytokines and immune modulators, include, at least, interferons of alpha, beta and gamma, and colony stimulating factors. However, other immune modulators are known and may be used, such as IL-1, IL-2, IL-3, IL-6, IL-10, IL-12, IL-18, TNF-$\alpha$, stem cell growth factors, lymphotoxins, erythropoietin, thrombopoietin, G-CSF, GM-CSF, S1 factor or a combination thereof.

Alternative embodiments concern methods for the intravascular identification of HIV-infected tissues, in a subject by administering an effective amount of a HIV targeting molecule and a targetable construct. The HIV targeting molecule comprises at least one ABS that specifically binds to an HIV antigen, and at least one ABS that specifically binds a targetable construct.

Kits

Some embodiments concern kits for practicing the claimed methods. The kit may include an HIV targeting molecule. The targeting molecule may be labeled by any of the agents described above. Further, the targeting molecule may be unlabeled but the kit may comprise labeling reagents to label the targeting molecule. The labeling reagents, if included, may contain the label and a crosslinker. The kit may also contain a HIV targeting molecule comprising at least one antibody specific for an HIV antigen and at least one antibody specific for a carrier. The kit may optionally contain a clearing composition to remove HIV targeting molecule from circulation.

The kit components may be packaged together or separated into two or more separate containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

Methods of Disease Tissue Detection, Diagnosis and Imaging

In Vivo Diagnosis

Anti-HIV antibodies or fragments are of use for in vivo diagnosis. Methods of diagnostic imaging with labeled Mabs are well-known. For example, in the technique of immunoscintigraphy, anti-HIV antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as fluorine-18 ($^{18}F$), gallium-68 ($^{68}Ga$), and iodine-124 ($^{124}I$). Such imaging can be conducted by direct labeling of the anti-HIV antibody or fragment, or by a pretargeted imaging method, as described in Goldenberg et al., 2006, J. Clin. Oncol. 24:823-34; see also U.S. Patent Publication Nos. 20050002945, 20040018557, 20030148409 and 20050014207, each incorporated herein by reference.

For diagnostic imaging, radioisotopes may be bound to the anti-HIV antibody or fragment either directly or indirectly by using an intermediary functional group. Useful intermediary functional groups include chelators such as ethylenediaminetetraacetic acid and diethylenetriaminepentaacetic acid. For example, see Shih et al., supra, and U.S. Pat. No. 5,057,313.

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that can be bound to anti-HIV antibody and are appropriate for diagnostic imaging include $^{99m}Tc$ and $^{111}In$.

The anti-HIV antibody or fragments thereof also can be labeled with paramagnetic ions and a variety of radiological contrast agents for purposes of in vivo diagnosis. Contrast agents that are particularly useful for magnetic resonance imaging comprise gadolinium, manganese, dysprosium, lanthanum, or iron ions. Additional agents include chromium, copper, cobalt, nickel, rhenium, europium, terbium, holmium, or neodymium. Anti-HIV antibody or fragments thereof can also be conjugated to ultrasound contrast/enhancing agents. For example, one ultrasound contrast agent is a liposome that comprises a humanized anti-HIV IgG or fragment thereof. Also preferred, the ultrasound contrast agent is a liposome that is gas filled.

In a preferred embodiment, a bispecific antibody can be conjugated to a contrast agent. For example, the bispecific antibody may comprise more than one image-enhancing agent for use in ultrasound imaging. In a preferred embodiment, the contrast agent is a liposome. Preferably, the liposome comprises a bivalent DTPA-peptide covalently attached to the outside surface of the liposome. Still more preferred, the liposome is gas filled.

Imaging Agents and Radioisotopes

In certain embodiments, the claimed peptides or proteins may be attached to imaging agents of use for imaging and diagnosis of various diseased organs, tissues or cell types. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$carbon, $^{51}$chromium, $^{36}$chlorine, $^{57}$cobalt, $^{58}$cobalt, copper$^{62}$, copper$^{64}$, copper$^{67}$, $^{152}$Eu, fluorine$^{18}$, gallium$^{67}$, gallium$^{68}$, $^{3}$hydrogen, iodine$^{123}$, iodine$^{124}$, iodine$^{125}$, iodine$^{131}$, indium", $^{52}$iron, $^{59}$iron, $^{32}$phosphorus, $^{33}$phosphorus, rhenium$^{186}$, rhenium$^{188}$, Sc$^{47}$, $^{75}$selenium, silver", $^{35}$sulphur, technicium$^{94m}$ technicium$^{99m}$ yttrium$^{86}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides may be labeled with technetium$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as $SNCl_2$, a buffer solution such as sodium-potassium phthalate solution, and the peptide. Intermediary functional groups which are often used to bind radioisotopes which exist as metallic ions to peptides include diethylenetriaminepentaacetic acid (DTPA), DOTA, NOTA, porphyrin chelators and ethylene diaminetetracetic acid (EDTA). Also contemplated for use are fluorescent labels, including rhodamine, fluorescein isothiocyanate and renographin.

In certain embodiments, the anti-HIV antibodies or fragments may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference. These fluorescent labels are preferred for in vitro uses, but may also be of utility in in vivo applications, particularly endoscopic or intravascular detection procedures.

In alternative embodiments, anti-HIV antibody or fragments may be tagged with a fluorescent marker. Non-limiting examples of photodetectable labels include Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red. These and other luminescent labels may be obtained from commercial sources such as Molecular Probes (Eugene, Oreg.).

Chemiluminescent labeling compounds of use may include luminol, isoluminol, an aromatic acridinium ester, an imidazole, an acridinium salt and an oxalate ester, or a bioluminescent compound such as luciferin, luciferase and aequorin.

In various embodiments, labels of use may comprise metal nanoparticles. Methods of preparing nanoparticles are known. (See e.g., U.S. Pat. Nos. 6,054,495; 6,127,120; 6,149,868; Lee and Meisel, *J. Phys. Chem.* 86:3391-3395, 1982.) Nanoparticles may also be obtained from commercial sources (e.g., Nanoprobes Inc., Yaphank, N.Y.; Polysciences, Inc., Warrington, Pa.). Modified nanoparticles are available commercially, such as NANOGOLD® (gold nanoparticles) from Nanoprobes, Inc. (Yaphank, N.Y.). Functionalized nanoparticles of use for conjugation to proteins or peptides may be commercially obtained.

Cross-Linkers

In some embodiments, anti-HIV antibodies or fragments or other HIV targeting molecules may be labeled using various cross-linking reagents known in the art, such as homo-bifunctional, hetero-bifunctional and/or photoactivatable cross-linking reagents. Non-limiting examples of such reagents include bisimidates; 1,5-difluoro-2,4-(dinitrobenzene); N-hydroxysuccinimide ester of suberic acid; disuccinimidyl tartarate; dimethyl-3,3'-dithio-bispropionimidate; N-succinimidyl-3-(2-pyridyldithio)propionate; 4-(bromoaminoethyl)-2-nitrophenylazide; and 4-azidoglyoxal. In an exemplary embodiment, a carbodiimide cross-linker, such as DCCD or EDC, may be used to cross-link acidic residues to amino or other groups. Such reagents may be modified to attach various types of labels, such as fluorescent labels.

Bifunctional cross-linking reagents have been extensively used for a variety of purposes. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described (U.S. Pat. No. 5,889,155, incorporated herein by reference). The cross-linking reagents combine a nucleophilic hydrazide residue with an electrophilic maleimide residue, allowing coupling in one example, of aldehydes to free thiols. The cross-linking reagent can be modified to cross-link various functional groups.

EXAMPLES

The following examples are included to demonstrate preferred embodiments of the invention. It should be appreciated by those of skill in the art that the techniques disclosed in the examples which follow represent techniques discovered to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Inhibition of HIV Infection In Vitro and In Vivo Using Conjugated Anti-HIV Antibodies Summary To demonstrate the efficacy of an immunoconjugate against HIV-1, murine monoclonal antibody (Mab) against the envelope antigen of HIV (P4/D10) was conjugated with the conventional anti-cancer drug, doxorubicin, and tested against infectious virus and infected cells, both in vitro and in vivo. P4/D10 antibody was incubated with free virus (neutralization) or HIV-infected cells (inhibition) and the resulting infection was measured by a p24 capture enzyme-linked immunosorbent assay. In an HIV-1/MuLV mouse challenge model the ability of the conjugate to inhibit infection in vivo was measured.

Doxorubicin-conjugated P4/D10 neutralized HIV-$1_{IIIB}$ and eliminated intercellular spread and HIV replication in infected Jurkat cells in vitro. It also protected mice from challenge with HIV-$1_{IIIB}$/MuLV at an eight-fold lower concentration than needed for free antibody, whereas no effects were observed for free drug or irrelevant conjugate controls.

These results demonstrate that doxorubicin was concentrated to HIV-infected cells by the P4/D10 antibody, significantly (p=0.0001) contributing to HIV elimination. The same compositions and methods are of use to eradicate remaining antigen-expressing T-cells in patients treated with ART (anti-retroviral therapy).

In this study, we conjugated doxorubicin, an anticancer anthracycline with known pharmacology, toxicology, and antitumor activity in patients, to a neutralizing and ADCC-mediating monoclonal antibody (Mab) developed against the HIV-1 outer envelope gp120 (third variable loop region).

The P4/D10 antibody conjugated to doxorubicin was tested in vitro for its efficacy in eliminating HIV-1-infected cells among non-infected cells and in a mouse model by removing HIV-1/MuLV (murine leukemia virus) infected syngeneic cells from the intraperitoneal cavity. The anti-gp120 antibody, P4/D10, neutralizes HIV-1 virus and mediates ADCC (Broliden et al., 1990). It has also been used in its unconjugated form in a phase-I clinical trial for late-stage HIV-1 infected individuals, where it decreased HIV antigens for an extended period of time (Hinkula et al., 1994). The present study was the first to examine the combination of P4/D10 in a drug-conjugated form in a preclinical HIV model, in comparison to free Mab, free drug, and the irrelevant antibodies hRS7 (Stein et al., *Int J Cancer* 1993, 55:938-946) and hLL1 Griffiths et al., *Clin Cancer Res* 2003, 9:6567-6571; Sapra et al., *Clin Cancer Res* 2005, 11:5257-5264), that were conjugated similarly with doxorubicin.

Materials and Methods

Antibodies and Drug Conjugation.

Conjugation of doxorubicin with the IgG1K anti-gp120 antibody P4/D10 (Broliden et al., 1990) and the control antibodies, as well as the preparation of the bifunctional doxorubicin hydrazone derivative with a maleimide group, were performed according to Griffiths et al. (2003). Briefly, antibodies P4/D10, hLL1 (humanized anti-CD74), and hRS7 (humanized anti-EGP-1) in a final concentration of approximately 9 mg/ml, were mildly reduced with DTT (dithiothreitol) in PBS (pH 7.5) containing 5 mM EDTA, using about 2.2 mM final DTT concentration, corresponding to a 38-fold molar excess of the reductant with respect to the antibodies. The solutions were incubated at 37° C. for 40 min. The reduced Mabs were purified on spin-columns of Sephadex G50/80 in 50 mM sodium acetate buffer containing 150 mM NaCl and 2 mM EDTA (pH 5.3). The number of thiol groups generated on the antibodies was determined by Ellman's assay. For conjugation, mildly reduced antibodies at 6.5 mg/ml were mixed with the bifunctional doxorubicin. The incubates were kept on ice for 15 min, and purified on spin columns of G50/80 in 0.1 M sodium acetate (pH 6.5), followed by passage through a short column of Bio-Beads SM2 (Bio-Rad, Hercules, Calif.) equilibrated in the same buffer. The products were analyzed for doxorubicin/Mab substitution ratios by measuring absorbance. Size-exclusion HPLC analyses were performed on an analytical BioSil 250 column.

A GMP-produced lot of IgG from HIV infected patients (HIVIgG) (Guay et al. *AIDS* 2002, 16:1391-1400) was used as positive control and sera from HIV-negative individuals as negative controls. Free doxorubicin, as well as the anticancer humanized Mabs LL1 and RS7, similarly conjugated with doxorubicin, were included as controls for the conjugated P4/D10 antibody.

HIV-1 Neutralization Assay.

Doxorubicin P4/D10, unlabelled P4/D10, HIV immunoglobulin (HIVIgG), and HIV-negative serum were mixed with the HIV-1 isolate HIV-$1_{IIIB}$ (LAI) and incubated for 1 h at 37° C. before 50,000 Jurkat T-cells/well were added. After 1 h of incubation, the cells were washed with medium and new complete medium added (200 μl/well). After 7 days of culture, the amount of p24 produced was measured by a p24 capture ELISA (enzyme-linked immunosorbent assay) and the percent inhibition of HIV-1 p24 production was calculated.

HIV-1 Inhibition In Vitro.

Jurkat T-cells were infected with HIV-$1_{IIIB}$ by mixing 5-10×$10^6$ cells with 100× $TCID_{50}$ HIV-$1_{IIIB}$ and incubating for 1 h at 37° C. The cells were washed in medium and incubated at 37° C. Every third day, medium was changed and supernatant checked for p24 production. When close to 100% of the cells were infected, different proportions of HIV-$1_{IIIB}$-infected cells were mixed with uninfected cells. The cells were treated with serial dilutions of antibodies, serum, or free doxorubicin from 100 to 0.00001 μg/ml. After seven days of culture at 37° C., HIV-1 p24 inhibition was measured and supernatants from cells previously treated with 0.1-10 μg/ml of doxorubicin-P4/D10, unconjugated P4/D10, and 0.05-0.5 mg/ml HIV-negative serum were collected and transferred to fresh Jurkat T-cells to test if infectious HIV was identified by the p24 ELISA at days 3, 7, 10, 12, and 15 after initiation of the culture.

HIV-1/MuLV Challenge Model.

A human T-cell line, CEM-1B, with a genetically integrated MuLV genome was infected with HIV-$1_{IIIB}$, which led to the production of pseudoviruses with the HIV-1 genome and the MuLV envelope (Adang et al., PNAS USA 1999, 96:12749-753; Hinkula et al., *Cells Tissues Organs* 2004, 177:169-184). These virus supernatants were used to infect splenocytes from C57Bl/6×DBA F1 $K^{b/d}$ mice transgenic for HLA-A201. Isogenic mice were challenged with HIV-$1_{IIIB}$/MuLV infected splenocytes i.p. and were immediately given conjugated antibodies, free antibodies or free doxorubicin i.p. Ten days after challenge, mice were sacrificed and peritoneal cells collected. Peritoneal cells were pelleted and added to 1×$10^6$ HIV susceptible Jurkat T-cells or human PBMC grown in 24-well plates. From these secondary cultures, supernatant was removed and fresh medium added every 3-4 days. The amount of infectious HIV recovered in the supernatant was measured for 3 weeks by p24 ELISA.

Statistical Analysis.

To compare the in vitro HIV-1 neutralizing capacities of the anti-gp120 Mabs and control antibodies, Student's t-test and the non-parametric Kruskal-Wallis test were used. Statistical comparisons between the groups of mice treated with different antibodies were performed using the nonparametric Mann-Whitney U and Kruskal-Wallis tests. A difference was considered significant when a p-value of <0.05 was obtained. A non-parametric one-way ANOVA test was performed using GraphPad Prism version 4.0a (GraphPad Software, San Diego, Calif.) and was used for comparisons of HIV-1 isolation and p24 antigen positivity between the study groups.

Results

The number of thiol groups generated on the respective antibodies by mild reduction, as well as the doxorubicin/Mab substitution ratios in the final purified conjugates, ranged between 8.8 (P4/D10, hRS7) and 9.4 (hLL1), giving a ratio of approximately 9 drug molecules per IgG. High-pressure liquid chromatographic analyses showed that the conjugates and the native Mabs possessed similar retention times, with zero to minimal aggregation (data not shown).

No significant difference in HIV-1 neutralizing capacity of free HIV-1 virus (FIG. 1A) could be shown between the doxorubicin-conjugated P4/D10 Mab and either unconjugated P4/D10 Mab or the HIVIgG antibodies. However, all anti HIV-1 specific antibodies were significantly better then the negative control serum (p=0.001) at neutralizing HIV-$1_{IIIB}$.

When 3% HIV-$1_{IIIB}$ infected Jurkat cells were mixed with 97% uninfected cells, doxorubicin-P4/D10 mediated a significantly (p=0.002) stronger inhibition of intercellular spread of HIV-1 infection than free P4/D10, doxorubicin-conjugated control antibody, hLL1, or free doxorubicin at a concentration of 0.5 or 0.05 μg/ml (FIG. 1B). Similar results were seen at all other concentrations of infected and uninfected cells. It was of particular interest that the intercellular spread of infection appeared to be inhibited even more potently than the effect obtained with doxorubicin-P4/D10 as a neutralizing agent. Also, no infectious virus could be found in the cultures treated with high doses of doxorubicin-P4/D10, since no p24 production was detected after transfer of supernatants from these cell cultures to uninfected Jurkat cells (data not shown). The significant difference in effect between doxorubicin-P4/D10 and unconjugated P4/D10 could not have been predicted from the results on neutralization of free HIV-1 virus (FIG. 1A).

Figure 2:
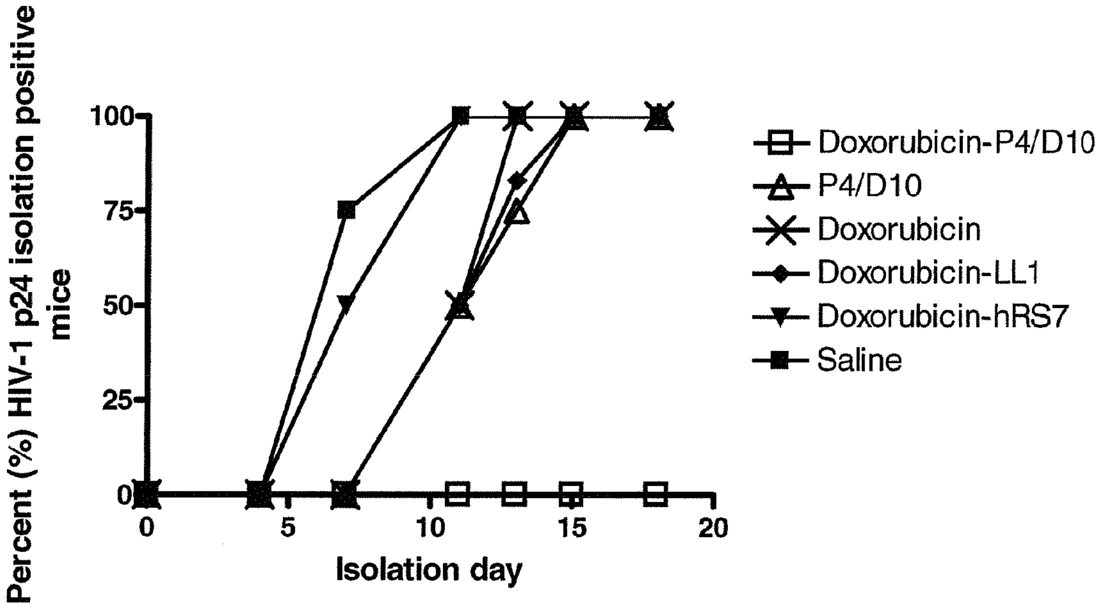
FIG. 2. Protection against HIV-1/MuLV infection in vivo. Mice (6-12/group) were challenged i.p. with HIV-1/MuLV infected splenocytes and immediately treated with monoclonal antibodies (Mab) or free doxorubicin. Unconjugated P4/D10 Mab was titrated 100-800 μg per mouse, free doxorubicin 100-400 μg and irrelevant doxorubicin-hRS7 100-200 μg. All other treatments were given at 100 μg per mouse. Ten days after challenge, peritoneal cells were collected and mixed with HIV susceptible Jurkat T-cells. HIV p24 production in these cell cultures was measured every 3-4 days for 18 days. Percent of mice with a p24 positive cell culture after treatment with 100 μg of Mab or free doxorubicin is shown. Only cells from mice treated with 100 μg doxorubicin-P4/D10 contained no infectious HIV, which was significantly different (p=0.0001) from all other groups.

To test the efficacy of doxorubicin-P4/D10 antibody in vivo, mice were given isogeneic HIV/MuLV-infected cells together with conjugates intraperitoneally. Peritoneal cells were harvested 10 days later and infectious HIV was demonstrated in all controls, similar to previous studies (Hinkula et al., 2004). The doxorubicin-P4/D10 antibody protected mice completely against challenge with HIV-1 infected primary lympoid cells (p=0.0001) (FIG. 2). No infectious HIV was recovered from peritoneal cells after challenge and treatment with 100 μg of doxorubicin-P4/D10 antibody. When mice were treated with 100 μg of unconjugated P4/D10 antibody, all were positive for p24 production. Complete protection by antibody alone was seen only when the dose was increased eight-fold, to 800 μg unconjugated P4/D10 per mouse. None of the doxorubicin-conjugated control antibodies (hLL1 or hRS7) provided any protection at doses of 100-200 μg, nor did doses of 100-400 μg of free doxorubicin.

Discussion

The results above show that the total virus-inhibiting properties of an antibody directed against the envelope of HIV-1 could be amplified significantly by coupling to doxorubicin. Doxorubicin-P4/D10 was capable of eliminating HIV-1 infected cells in vitro, as well as in an experimental in vivo challenge model. The ability of the unconjugated P4/D10 Mab to mediate ADCC against HIV-1 infected target cells as well as neutralizing HIV-1 (Broliden et al., 1990; Hinkula et al., 1994) may enhance its efficacy as a drug immunoconjugate in a non-toxic manner.

An anticancer anti-CD74 Mab, LL1, conjugated similarly to doxorubicin, has at very low doses shown remarkable activity in vitro and in human xenograft models of non-Hodgkin's lymphoma or multiple myeloma (Griffiths et al., 2003; Sapra et al., 2005). These studies, as well as toxicology in monkeys, indicated that only very high doses of the immunoconjugate would result in evidence of bone marrow suppression, but no cardiac toxicity related to doxorubicin was observed (Sapra et al., 2005). To avoid virus escape, antibodies directed against both conserved and variable sites of accessible epitopes of HIV should be tested together (Trkola et al., 2005; Ferrantelli et al., *J Infect Dis* 2004, 189:2167-2173).

In previous in vitro studies, HIV-1 specific immunoglobulins conjugated to *Pseudomonas* exotoxin A (PE40) removed HIV-1 infected cells (Pincus et al., 2003; Ashorn et al., *Proc Natl Acad Sci USA* 1990, 87:8889-8893). However, in clinical trials, PE40 coupled to CD4 cells proved to be immunogenic and hepatotoxic (Davey et al., 1994; Ramachandran et al., 1994). Thus, the present results, showing efficacy of a doxorubicin-Mab conjugate with little or no side effects, are surprising and unexpected. The toxicity of PE40-CD4 might be explained by formation of toxic complexes with free gp120, which is present in high concentrations in non-ART treated patients with high viral load (Berger et al., 1998). In order to avoid potential toxicity problems associated with high viral loads, molecules targeting HIV-envelope-specific epitopes should preferably be used in the setting when viral burden is low, such as during ART, early in HIV infection or even shortly after a known or potential exposure to infection with HIV. For example, health care workers exposed to accidental needle stick with HIV-contaminated or potentially contaminated blood or other fluids may be treated with a conjugated antibody according to the disclosed methods. As a result of the anticellular activity of the doxorubicin-P4/D10 conjugate, the addition of a drug conjugate to patients treated with ART may eliminate antigen-carrying cells as well as free virions, and thus reduce the viral load even further. The skilled artisan will realize that the claimed compositions and methods are not limited to a doxorubicin conjugate of P4/D10, but rather may utilize other known cytotoxic agents conjugated to P4/D10 or to other known anti-HIV antibodies.

In other embodiments, in order to avoid non-specific toxicity, bispecific antibodies and other pretargeting strategies may be used, in which antibody targeting and delivery of the toxic agent are separated (Wu et al., 2005). This strategy has shown promising results both in preclinical and in clinical cancer trials (Forero et al., *Blood* 2004, 104:227-236; Rossi et al., *Clin Cancer Res* 2005, 11:7122s-7129s). For in vivo use in human subjects, human or humanized forms of antibody for repeated clinical use are preferred.

Example 2

Treatment of an HIV-Infected Patient Following ART

A 47-year old male patient is determined to be seropositive for HIV. The patient has a CD4 count of less than 200/mm$^3$. The patient is treated with a standard regimen of the non-nucleoside reverse transcriptase inhibitor nevirapine. CD4 cell count improves to 300/mm$^3$, but the patient is still seropositive for HIV. The patient is treated with humanized doxorubicin-P4/D10 antibody. The patient's CD4 count improves to over 350/mm$^3$ and the patient is no longer seropositive for HIV. One year later, the patient remains asymptomatic and there is no detectable presence of HIV infection.

Example 3

Treatment of a Health Care Worker after Accidental Needle Stick

A 30-year old nurse practitioner is exposed to an accidental needle stick with HIV positive blood. Within 1 hour, the subject is treated with humanized doxorubicin-P4/D10 antibody. One year later, there is no sign of HIV infection in the subject.

Example 4

Treatment with Other Cytotoxins and/or Antibodies

A 28-year old male patient is determined to be seropositive for HIV. The patient has a CD4 count of less than 200/mm$^3$. The patient is treated with a standard regimen of the non-nucleoside reverse transcriptase inhibitor nevirapine. CD4 cell count improves to 300/mm$^3$, but the patient is still seropositive for HIV. The patient is treated with a bispecific antibody comprising a humanized 4E10 Fab-734 scFv, prepared using methods disclosed in U.S. Pat. No. 7,052,872 (incorporated herein by reference). A 24 hour incubation after injection was used to allow free bispecific antibody to clear from circulation, followed by injection of 5-fluorouracil conjugated to targeting peptide IMP-156 (Id.). The patient's CD4 count improves to over 350/mm$^3$ and the patient is no longer seropositive for HIV. One year later, the patient remains asymptomatic and there is no detectable presence of HIV infection.

Example 5

Pretargeting with IMP411

A 35-year old male patient is determined to be seropositive for HIV. The patient has a CD4 count of less than 180/mm$^3$. The patient is treated with a standard regimen of the non-nucleoside reverse transcriptase inhibitor nevirapine. CD4 cell count improves to 250/mm$^3$, but the patient is still seropositive for HIV. The patient is treated with a bispecific antibody comprising a bispecific anti-gp120 P4/D10 IgG1×Fab-679, prepared by the DNL technique using methods disclosed in U.S. patent application Ser. Nos. 11/389,358, 11/391,584, 11/478,021 and 11/633,729, incorporated herein by reference. A 24 hour incubation after injection was used to allow free bispecific antibody to clear from circulation, followed by injection of SN38 conjugated to targeting peptide IMP-411. The patient's CD4 count improves to over 325/mm$^3$ and the patient is no longer seropositive for HIV. One year later, the patient remains asymptomatic and there is no detectable presence of HIV infection.

Example 6

Humanization of Anti-HIV Antibody cDNAs encoding the VL and VH regions of a mouse monoclonal antibody against HIV envelope protein are isolated and separately recombinantly subcloned into mammalian expression vectors containing the genes encoding kappa and $IgG_1$ constant regions, respectively, of human antibodies. Cotransfection of mammalian cells with these two recombinant DNAs results in expression of a humanized Mab that has the same binding and therapeutic characteristics of the parent mouse Mab.

The CDRs of the VK and VH DNAs are recombinantly linked to the framework (PR) sequences of the human VK and VH regions, respectively, which are subsequently linked, respectively, to the human kappa and $IgG_1$ constant regions, so as to express in mammalian cells. Generally, as discussed herein, "chimeric" Mabs are formed by joining or subcloning murine VK and VH regions to human constant light and heavy chains, respectively, while "humanized" Mabs are further derivatized by replacing the murine framework (FR) sequences in the chimeric Mab with the corresponding human FR sequences. As discussed below, the humanized Mab may be further optimized by replacement of one or more human FR amino acids with corresponding murine FR amino acids, particularly for FR residues touching or close to the CDR amino acid residues.

In various embodiments, antibody variable domains can be modeled by computer modeling (see, for example, Dion, "Humanization of Monoclonal Antibodies: Molecular Approaches and Applications," in Goldenberg et al. eds., Cancer Therapy With Radiolabeled Antibodies, Ch. 19, CRC Press, Boca Raton, Fla., 1994), which is incorporated herein by reference. In general, the 3-D structure for Mabs are best modeled by homology, preferably following identification of human FR sequences showing high (over 75%, preferably over 85%, more preferably over 90%, more preferably over 95%) homology with the murine FR sequences to be replaced. Wherever possible, side group replacements should be performed so as to maintain the torsion angle between Cα and Cβ. Energy minimization may be accomplished by the AMBER forcefield (Weiner et al, J. Amer. Chem. Soc. 106: 765, 1984) using the convergent method. Potentially critical FR-CDR interactions can be determined by initially modeling the light and heavy variable chains. All murine FR residues within a 4.5 angstrom radius of all atoms within each CDR can thereby be identified and retained in the final design model of the humanized antibody.

Once the sequences for the VK and VH domains are designed, CDR engrafting can be accomplished by gene synthesis using long synthetic DNA oligonucleotides as templates and short oligonucleotides as primers in a PCR reaction. In most cases, the DNA encoding the VK or VH domain will be approximately 350 bp long. By taking advantage of codon degeneracy, a unique restriction site may easily be introduced, without changing the encoded amino acids, at regions close to the middle of the V gene DNA sequence. Two long non-overlapping single-stranded DNA oligonucleotides about 150 bp upstream and downstream of the restriction site can be generated by automated DNA oligonucleotide synthesizer (Cyclone Plus DNA Synthesizer, Milligen-Biosearch). As the yields of full length DNA oligonucleotides may be expected to be low, they can be amplified by two pairs of flanking primers in a PCR reaction.

The primers can be designed with the necessary restriction sites to facilitate subsequent subcloning. Primers for oligo A and for oligo B should contain overlapping sequence at the restriction site so that the resultant PCR product for oligo A and B, respectively, can be joined in-frame at the restriction site to form a full length DNA sequence (ca 350 bp) encoding the VH domain.

The ligation of the PCR products for oligo A and B and their subcloning into appropriate restriction sites of the staging vector can be completed in a single three-fragment-ligation step. The subcloning of the correct sequence into the staging vector can be first analyzed by restriction digestion analysis and subsequently confirmed by sequencing reaction according to Sanger et al., Proc. Natl. Acad. Sci. USA 74: 5463 (1977).

A restriction fragment containing the Ig promoter, leader sequence and the VH sequence can be excised from the staging vector and subcloned to the corresponding sites in a pSVgpt-based vector, which contains the genomic sequence of the human IgG constant region, an Ig enhancer and a gpt selection marker, forming the final expression vector. Similar strategies can be employed for the construction of the VK sequence.

The DNA sequence containing the Ig promoter, leader sequence and the anti-HIV VK sequence can be excised from the staging vector by treatment with appropriate endonucleases, and can be subcloned into the corresponding sites of a pSVhyg-based vector, pKh, which contains the genomic sequence of human kappa chain constant regions, a hygromycin selection marker, an Ig and a kappa enhancer, forming the final expression vector.

As humanization sometimes results in a reduction or even loss of antibody affinity, additional modification might be required in order to restore the original affinity (See, for example, Tempest et al., Bio/Technology 9: 266 (1991); Verhoeyen et al., Science 239: 1534 (1988)), which are incorporated by reference. In general, to prepare chimeric anti-HIV Mab, VH and VK chains of the anti-HIV Mab can be obtained by PCR cloning using DNA products and primers. Orlandi et al. (Proc. Natl. Acad. Sci., USA, 1989, 86: 3833), and Leung et al. (BioTechniques, 1993, 15:286). The VK PCR primers may be subcloned into a pBR327 based staging vector (VK-pBR) as described above. The VH PCR products may be subcloned into a similar pBluescript-based staging vector (VHpBS) as described above. The fragments containing the VK and VH sequences, along with the promoter and signal peptide sequences, can be excised from the staging vectors using appropriate restriction endonucleases. The VK fragments (about 600 bp) can be subcloned into a mammalian expression vector (for example, pKh) conventionally. pKh is a pSVhyg-based expression vector containing the genomic sequence of the human kappa constant region. an Ig enhancer, a kappa enhancer and the hygromycin-resistant gene. Similarly, the about 800 bp VH fragments can be subcloned into pG1g, a pSVgpt-based expression vector carrying the genomic sequence of the human IgG1 constant region, an Ig enhancer and the xanthine-guanine phosphoribosyl transferase (gpt) gene. The two plasmids may be transfected into mammalian expression cells, such as Sp2/O—Ag14 cells, by electroporation and selected for hygromycin resistance. Colonies surviving selection are expanded, and supernatant fluids monitored for production of chimeric anti-HIV Mab by an ELISA method. A transfection efficiency of about 1-10×$10^6$ cells is desirable. An antibody expression level of between 0.10 and 2.5 μg/ml can be expected with this system.

RNA isolation, cDNA synthesis, and amplification can be carried out as follows. Total cell RNA can be prepared from a anti-HIV hybridoma cell line, using a total of about $10^7$ cells, according to Sambrook et al., (Molecular Cloning: A Laboratory Manual, Second ed., Cold Spring Harbor Press, 1989), which is incorporated by reference. First strand cDNA can be reverse transcribed from total RNA conventionally, such as by using the SuperScript preamplification system (Gibco/BRL., Gaithersburg, Md.). Briefly, in a reaction volume of 20 µl, 50 ng of random primers can be annealed to 5 µg of RNAs in the presence of 2 µl of 10× synthesis buffer [200 mM Tris-HCl (pH 8.4), 500 mM KCl, 25 mM $MgCl_2$, 1 mg/ml BSA], 1 µl of 10 mM dNTP mix, 2 µl of 0.1 M DTT, and 200 units of SuperScript reverse transcriptase. The elongation step is initially allowed to proceed at room temperature for 10 mM followed by incubation at 42° C. for 50 mM. The reaction can be terminated by heating the reaction mixture at 90° C. for 5 mM.

The VK and VH sequences for chimeric or human anti-HIV Mab can amplified by PCR as described by Orlandi et al., (Proc. Natl. Acad. Sci., USA, 86: 3833 (1989)) which is incorporated by reference. VK sequences may be amplified using the primers CK3BH and VK5-3 (Leung et al., BioTechniques, 15: 286 (1993), which is incorporated by reference), while VH sequences can be amplified using the primer CH1B which anneals to the CH1 region of murine IgG, and VHI-BACK (Orlandi et al., 1989). The PCR reaction mixtures containing 10 µl of the first strand cDNA product, 9 µl of 10× PCR buffer [500 mM KCl, 100 mM Tris-HCl (pH 8.3), 15 mM MgCl2, and 0.01% (w/v) gelatin] (Perkin Elmer Cetus, Norwalk, Conn.), can be subjected to 30 cycles of PCR. Each PCR cycle preferably consists of denaturation at 94° C. for 1 min, annealing at 50° C. for 1.5 min, and polymerization at 72° C. for 1.5 min. Amplified VK and VH fragments can be purified on 2% agarose (BioRad, Richmond, Calif.).

PCR products for VK can be subcloned into a staging vector, such as a pBR327-based staging vector VKpBR that contains an Ig promoter, a signal peptide sequence and convenient restriction sites to facilitate in-frame ligation of the VK PCR products. PCR products for VH can be subcloned into a similar staging vector, such as the pBluescript-based VHpBS. Individual clones containing the respective PCR products may be sequenced by, for example, the method of Sanger et al., Proc. Natl. Acad. Sci., USA, 74: 5463 (1977) which is incorporated by reference.

The two plasmids can be co-transfected into an appropriate cell, e.g., myeloma Sp2/O—Ag14, colonies selected for hygromycin resistance, and supernatant fluids monitored for production of chimeric or humanized anti-HIV antibodies by, for example, an ELISA assay.

Transfection and assay for antibody secreting clones by ELISA, can be carried out as follows. About 10 µg of light chain expression vector and 20 µg of heavy chain expression vector can be used for the transfection of $5\times10^6$ SP2/O myeloma cells by electroporation (BioRad, Richmond, Calif.) according to Co et al., J. Immunol., 148: 1149 (1992) which is incorporated by reference. Following transfection, cells may be grown in 96-well microtiter plates in complete HSFM medium (GIBCO, Gaithersburg, Md.) at 37° C., 5% $CO_2$. The selection process can be initiated after two days by the addition of hygromycin selection medium (Calbiochem, San Diego, Calif.) at a final concentration of 500 µg/ml of hygromycin. Colonies typically emerge 2-3 weeks post-electroporation. The cultures can then be expanded for further analysis.

Transfectoma clones that are positive for the secretion of chimeric or humanized heavy chain can be identified by ELISA assay. Briefly, supernatant samples (100 µl) from transfectoma cultures are added in triplicate to ELISA microtiter plates precoated with goat anti-human (GAH)-IgG, $F(ab')_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch, West Grove, Pa.) are added to the wells, (100 µl of antibody stock diluted$\times10^4$, supplemented with the unconjugated antibody to a final concentration of 1.0 µg/ml). Following an incubation of 1 h, the plates are washed, typically three times. A reaction solution, [100 µl, containing 167 µg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 µl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 micron membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 µl of 3 M Tris(pH 8.6), and protein concentrations determined from the absorbancies at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

Comparative binding affinities of the mouse, chimeric and humanized antibodies thus isolated may be determined by direct radioimmunoassay. The chimeric and humanized anti-HIV antibodies are determined to have the same binding specificity and affinity as the mouse Mab.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A pharmaceutical composition comprising a P4/D10 antibody or fragment thereof against an HIV surface envelope antigen, the antibody or fragment conjugated to a cytotoxic drug, wherein exposure to the conjugated antibody or fragment is effective to reduce HIV infection or to limit the intercellular transmission of HIV to uninfected cells when administered to a subject.

2. The composition of claim 1, wherein the subject is a human subject.

3. The composition of claim 1, wherein the conjugated antibody or fragment is a chimeric, humanized or human antibody or fragment.

4. The composition of claim 1, wherein the cytotoxic drug is doxorubicin.

5. The composition of claim 1, wherein the cytotoxic drug is aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, doxorubicin, 2-pyrrolinodoxorubicine (2P-DOX), cyano-morpholino doxorubicin, doxorubicin glucuronide, epirubicin glucuronide, estramustine, etoposide, etoposide glucuronide, etoposide phosphate, floxuridine (FUdR), 3',5'-O-dioleoyl-FudR (FUdR-dO), fludarabine, flutamide, fluorouracil, gemcitabine, hydroxyurea, idarubicin, Ifosfamide, L-asparaginase, leucovorin, lomustine, mechlorethamine, melphalan, mercaptopurine, 6-mercaptopurine, methotrexate, mitoxantrone, mithramycin, mitomycin, mitotane, phenyl butyrate, procarbazine, paclitaxel, pentostatin, PSI-341, semustine, streptozocin, tamoxifen, taxanes, taxol, thalidomide, thioguanine, thiotepa, teniposide, topotecan, uracil mustard, velcade, vinblastine, vinorelbine, vincristine or a combination thereof.

6. The composition of claim 1, wherein the antibody or fragment is a bispecific antibody, a bispecific antibody fragment, an scFv, a Fab, a Fab', a $F(ab)_2$, a $F(ab')_2$, an Fv, an sFv, an scFv, an scFv-Fc fusion, a single chain antibody, a diabody, a triabody or a tetrabody.

7. The composition of claim 1, wherein the antibody or fragment is a neutralizing antibody.

8. The composition of claim 1, further comprising a second antibody or fragment thereof, wherein the second antibody or fragment binds to an HIV surface envelope antigen.

9. The composition of claim 8, wherein the second antibody or fragment binds to the same HIV surface envelope antigen as the P4/D10 antibody.

10. The composition of claim 8, wherein the second antibody or fragment binds to a different HIV surface envelope antigen than the P4/D10 antibody.

11. The composition of claim 8, wherein the second antibody or fragment thereof is selected from the group consisting of 4E10, 2F5, 3D6, C37, 1ACY, 1F58, 1GGGC, 2G12 and X5.

12. The composition of claim 1, further comprising an anti-retroviral agent selected from the group consisting of efavirenz, zidovudine, tenofovir, lamivudine, emtricitabine, didanosine, abacavir, stavudine, nevirapine, lopinavir, ritonavir, atazanavir, fosamprenavir, indinavir, nelfinavir and saquinavir.

13. The composition of claim 1, wherein exposure to the conjugated antibody or fragment is effective to reduce HIV infection or to limit the intercellular transmission of HIV to uninfected cells in vivo.

14. The composition of claim 1, wherein the conjugated antibody or fragment thereof is a bispecific antibody or fragment thereof.

15. The composition of claim 14, wherein the bispecific antibody further comprises a second antibody or fragment thereof and the second antibody or fragment thereof binds to a hapten on a targetable construct.

16. The composition of claim 14, wherein the bispecific antibody or fragment comprises at least one scFv, Fab, Fab', $F(ab)_2$, $F(ab')_2$, Fv, sFv, scFv-Fc fusion, single chain antibody, diabody, triabody or tetrabody.

17. The composition of claim 15, wherein the hapten is HSG (histamine-succinyl-glycine) or In-DTPA.

18. The composition of claim 15, wherein the bispecific antibody or fragment comprises one or more 679 antibodies or antibody fragments that bind to HSG.

19. A pharmaceutical composition comprising an antibody or fragment thereof against an HIV surface envelope antigen, the antibody or fragment conjugated to a cytotoxic drug, wherein the antibody or fragment competes for binding to gp120 with the P4/D10 antibody, wherein exposure to the conjugated antibody or fragment is effective to reduce HIV infection or to limit the intercellular transmission of HIV to uninfected cells when administered to a subject.

20. The composition of claim 19, wherein the subject is a human subject.

21. The composition of claim 19, wherein the conjugated antibody or fragment is a chimeric, humanized or human antibody or fragment.

22. The composition of claim 19, wherein the cytotoxic drug is doxorubicin.

23. The composition of claim 19, wherein the cytotoxic drug is aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, doxorubicin, 2-pyrrolinodoxorubicine (2P-DOX), cyano-morpholino doxorubicin, doxorubicin glucuronide, epirubicin glucuronide, estramustine, etoposide, etoposide glucuronide, etoposide phosphate, floxuridine (FUdR), 3',5'-O-dioleoyl-FudR (FUdR-dO), fludarabine, flutamide, fluorouracil, gemcitabine, hydroxyurea, idarubicin, ifosfamide, L-asparaginase, leucovorin, lomustine, mechlorethamine, melphalan, mercaptopurine, 6-mercaptopurine, methotrexate, mitoxantrone, mithramycin, mitomycin, mitotane, phenyl butyrate, procarbazine, paclitaxel, pentostatin, PSI-341, semustine, streptozocin, tamoxifen, taxanes, taxol, thalidomide, thioguanine, thiotepa, teniposide, topotecan, uracil mustard, velcade, vinblastine, vinorelbine, vincristine or a combination thereof.

24. The composition of claim 19, wherein the antibody or fragment is a bispecific antibody, a bispecific antibody fragment, an scFv, a Fab, a Fab', a $F(ab)_2$, a $F(ab')_2$, an Fv, an sFv, an scFv, an scFv-Fc fusion, a single chain antibody, a diabody, a triabody or a tetrabody.

25. The composition of claim 19, wherein the antibody or fragment is a neutralizing antibody.

* * * * *